(12) United States Patent
Rees et al.

(10) Patent No.: US 10,159,603 B2
(45) Date of Patent: Dec. 25, 2018

(54) GOGGLES FOR SNOWSPORTS

(71) Applicant: RUROC IP HOLDINGS LIMITED, Gloucester (GB)

(72) Inventors: Daniel Rees, Gloucester (GB); Martin Knoepfli, Hong Kong (CN)

( * ) Notice: Subject to any disclaimer, the term of this patent is extended or adjusted under 35 U.S.C. 154(b) by 0 days.

(21) Appl. No.: 15/286,358

(22) Filed: Oct. 5, 2016

(65) Prior Publication Data

US 2017/0128267 A1    May 11, 2017

(30) Foreign Application Priority Data

Nov. 11, 2015    (GB) .................................... 1519880.7

(51) Int. Cl.
*A61F 9/02*    (2006.01)
*A61F 9/00*    (2006.01)

(52) U.S. Cl.
CPC ................. *A61F 9/029* (2013.01); *A61F 9/02* (2013.01); *A61F 9/025* (2013.01); *A61F 9/027* (2013.01)

(58) Field of Classification Search
CPC .... A61F 2210/009; A61F 9/02; A61F 2/1613; A61F 9/045; A42B 3/185; A42B 3/042; A42B 1/247; G02B 23/125; G02B 23/16; G02C 2200/08; G02C 2200/02; G02C 1/10; G02C 1/04; G02C 1/06; G02C 1/08; G02C 5/008; G02C 7/02; G02C 9/04; G02C 2200/06; G02C 5/22; G02C 5/2209; G02C 5/2263
See application file for complete search history.

(56) References Cited

U.S. PATENT DOCUMENTS

| 3,896,496 A | * | 7/1975 | Leblanc | .................. | A61F 9/025 |
| | | | | | 2/439 |
| 5,331,684 A | * | 7/1994 | Baril | .................... | G02B 23/125 |
| | | | | | 2/422 |
| 5,506,730 A | * | 4/1996 | Morley | .................... | A42B 3/04 |
| | | | | | 2/422 |

(Continued)

FOREIGN PATENT DOCUMENTS

WO    2014065528    5/2014

OTHER PUBLICATIONS

UK IPO Search Report dated Apr. 15, 2016 5 Pages.

*Primary Examiner* — Bobby Muromoto, Jr.
(74) *Attorney, Agent, or Firm* — The Roy Gross Law Firm, LLC; Roy Gross

(57) ABSTRACT

A goggle for use in snowsports including a flexible frame and a lens assembly, magnets or magnetic elements being provided on upper and lower edges of an inner surface of the lens assembly and magnets or magnetic elements being provided in corresponding positions on an outer surface of the frame, for releasably holding the lens assembly in the frame, and at least two releasable clips being provided on the frame, the clips being movable between a released position and an engaged position, the clips in the engaged position overlying a portion of the lens assembly and each clip including at least one retaining member which in use passes into an aperture at least part way through the lens assembly, in a direction substantially perpendicular to the surface of the lens assembly, for preventing or limiting movement of the lens assembly in a direction away from the lateral side of the frame.

16 Claims, 4 Drawing Sheets

(56) References Cited

U.S. PATENT DOCUMENTS

| | | | | |
|---|---|---|---|---|
| 7,370,961 B2* | 5/2008 | Lerner | G02C 9/00 | 351/47 |
| 8,016,415 B2* | 9/2011 | Figler | G02F 1/13452 | 351/121 |
| 8,375,473 B2* | 2/2013 | Celona | G02B 23/125 | 2/422 |
| 8,408,695 B2* | 4/2013 | Calilung | G02C 1/06 | 351/137 |
| 8,534,830 B2* | 9/2013 | Taylor | G02C 1/04 | 351/106 |
| 8,555,423 B2* | 10/2013 | Giroux | A42B 3/185 | 2/422 |
| 8,661,562 B2* | 3/2014 | Calilung | A61F 9/025 | 2/12 |
| 8,911,076 B2* | 12/2014 | Calilung | G02C 1/06 | 351/137 |
| 8,915,588 B2* | 12/2014 | Blum | G02C 11/10 | 348/838 |
| 9,116,355 B2* | 8/2015 | Teetzel | G02B 23/16 | |
| 9,122,078 B2* | 9/2015 | Calilung | G02C 5/22 | |
| 9,124,796 B2* | 9/2015 | Blum | A61F 2/1627 | |
| 9,302,382 B2* | 4/2016 | Tuohy, III | B25F 1/00 | |
| 9,539,144 B2* | 1/2017 | Dunleavy | A42B 3/185 | |
| 9,625,699 B2* | 4/2017 | Teetzel | G02B 23/18 | |
| 9,675,493 B2* | 6/2017 | Castillo | A61F 5/08 | |
| 9,717,631 B2* | 8/2017 | Cater | A61F 9/028 | |
| 9,720,255 B2* | 8/2017 | Park | G02C 9/04 | |
| 9,864,211 B2* | 1/2018 | Belbey | G02C 7/02 | |
| 2005/0225713 A1* | 10/2005 | Lerner | G02C 9/00 | 351/57 |
| 2007/0256214 A1* | 11/2007 | Mcgowan | A42B 1/247 | 2/209.13 |
| 2009/0251660 A1* | 10/2009 | Figler | G02F 1/13452 | 351/158 |
| 2010/0299814 A1* | 12/2010 | Celona | A42B 3/04 | 2/422 |
| 2011/0145981 A1* | 6/2011 | Teetzel | A42B 3/04 | 2/422 |
| 2011/0225709 A1* | 9/2011 | Saylor | A61F 9/025 | 2/431 |
| 2012/0134141 A1* | 5/2012 | Wright | F21L 4/045 | 362/103 |
| 2012/0167277 A1* | 7/2012 | Dunleavy | A42B 3/185 | 2/243.1 |
| 2012/0180203 A1* | 7/2012 | Giroux | A42B 3/185 | 2/422 |
| 2012/0324638 A1* | 12/2012 | Tobia | A61F 9/02 | 2/439 |
| 2013/0083391 A1* | 4/2013 | Teetzel | G02B 23/18 | 359/409 |
| 2013/0104300 A1* | 5/2013 | Park | A61F 9/025 | 2/439 |
| 2013/0185849 A1* | 7/2013 | Laughlin | A61F 9/025 | 2/431 |
| 2013/0250232 A1* | 9/2013 | Belbey | G02C 7/02 | 351/158 |
| 2014/0157521 A1* | 6/2014 | Tuohy, III | B25F 1/00 | 7/105 |
| 2014/0245523 A1* | 9/2014 | Teetzel | A42B 3/04 | 2/422 |
| 2015/0173933 A1* | 6/2015 | Castillo | A61F 5/08 | 606/204.45 |
| 2015/0182370 A1* | 7/2015 | Castillo | A61F 5/08 | 606/204.45 |
| 2015/0323779 A1* | 11/2015 | Teetzel | G02B 23/18 | 359/409 |
| 2017/0090514 A1* | 3/2017 | Byun | G06F 1/166 | |

* cited by examiner

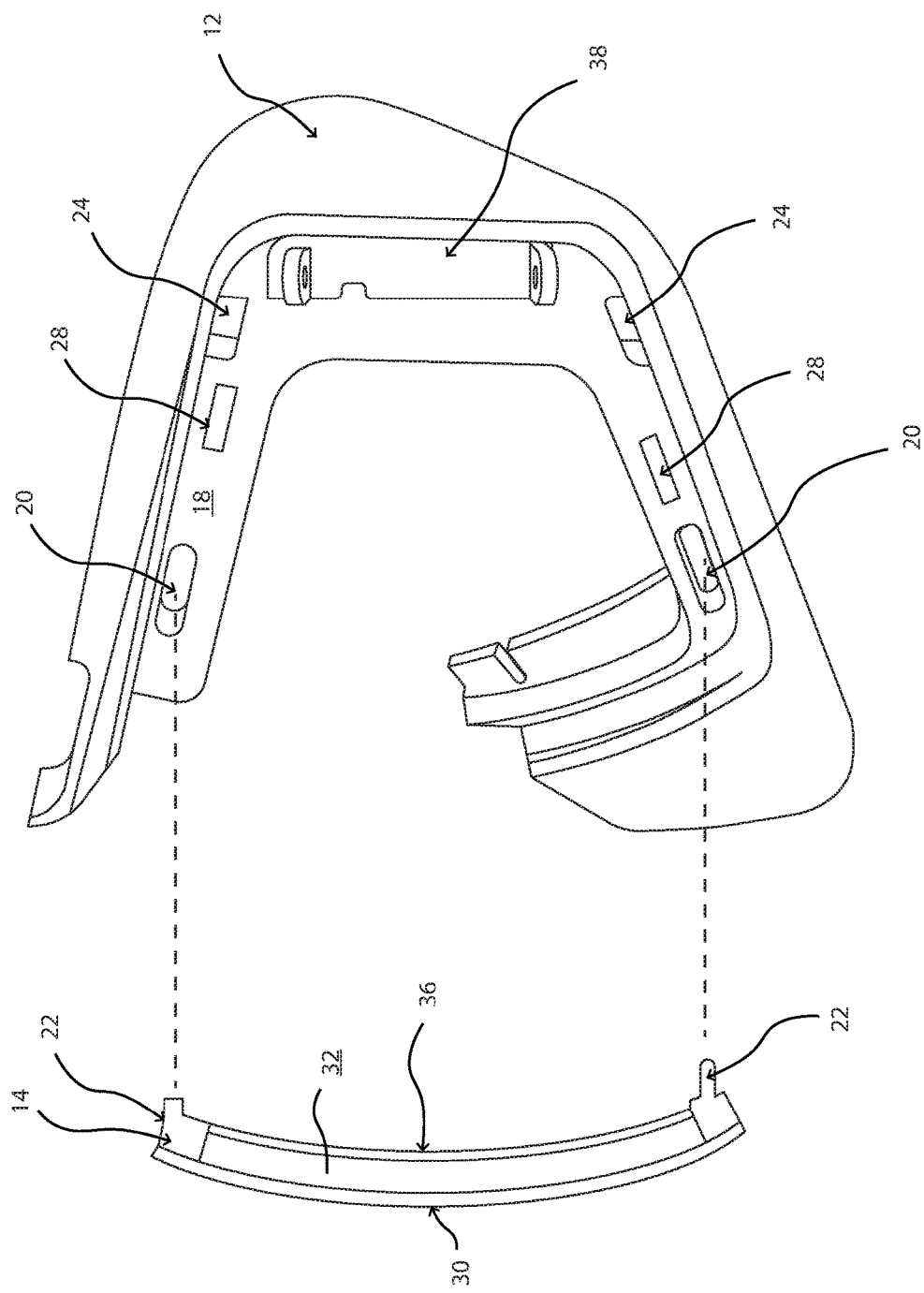

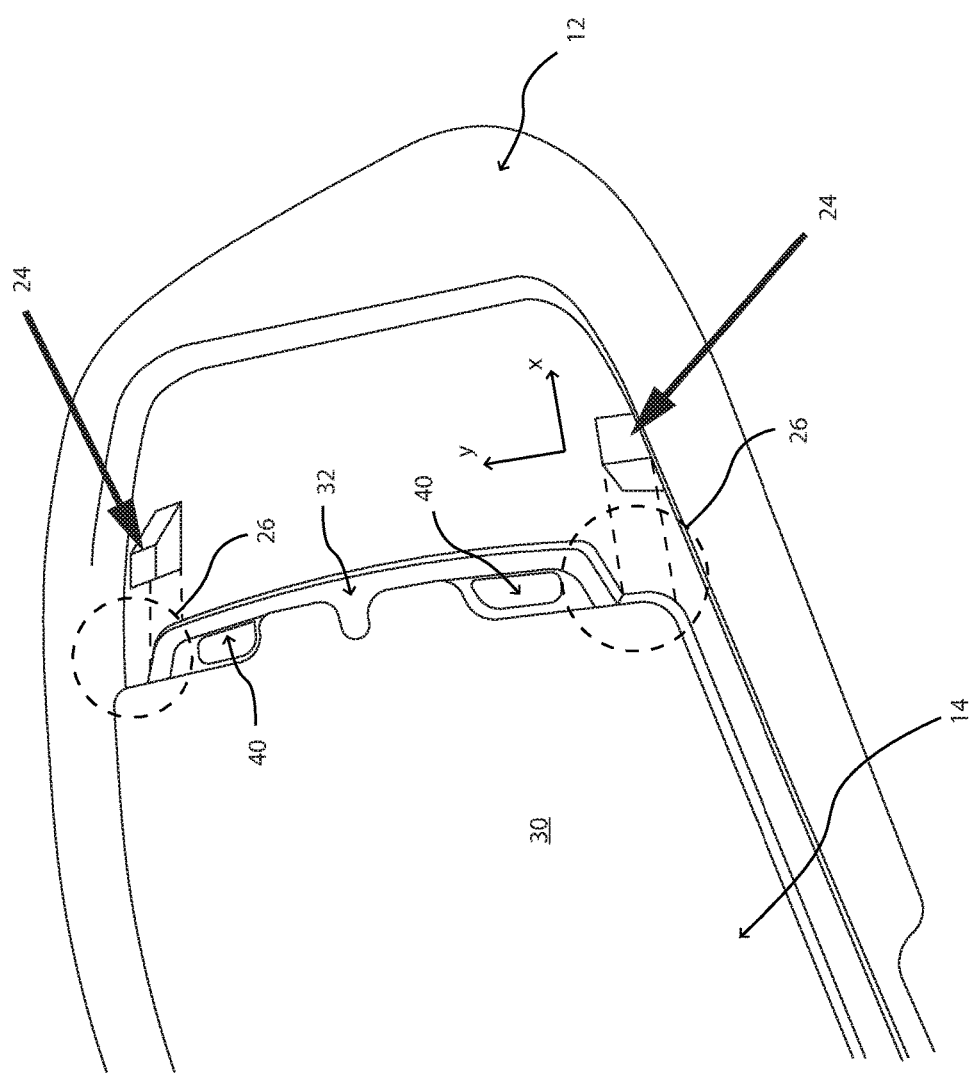

GOGGLES FOR SNOWSPORTS

FIELD OF THE INVENTION

The present invention relates to goggles, and in particular goggles suitable for use in snowsports, for example skiing and snowboarding.

BACKGROUND OF THE INVENTION

A wide range of different types of goggles are available for snowsports. In producing such a pair of goggles, there are a number of points which must be taken into consideration.

Falls and collisions are relatively common in snowsports, and goggles must be robust enough to stay intact and correctly positioned in most collisions. For this reason, it is common to make the frame of the goggle from a flexible plastics material, which can flex in response to external twisting forces. This makes the frame unlikely to crack or break in a collision.

The lens of the goggle is usually relatively rigid, and is generally made from polycarbonate. This material is highly resistant to impact, and has excellent UV-protection properties and optical clarity.

Lenses are available in different tints and colours, and different lenses are designed for the best performance in different weather conditions. A skier who skis in a range of different conditions will therefore want a range of different lenses. To avoid the bulk and expense of multiple pairs of goggles, goggles with interchangeable lenses are preferred, and preferably the lens is able to be swapped over as quickly and easily as possible.

Existing interchangeable lens systems include, for example, clips, magnets, or other releasable retaining means to keep the lens in place on the frame of the goggle. However, the problem with existing goggles is that providing a quick-release system for changing the lens means compromising on other factors. Goggles with a quick-release lens system tend to be more likely to come apart in a collision, which is inconvenient at best, but can also mean loss of an expensive lens, or even physical injury since the eyes will be unprotected once the lens falls away.

One common way of releasably attaching a lens to a frame is with magnets around the inner rim of the lens, which attract magnets or magnetic elements on the frame. However, as well as being prone to failure in a collision, this type of goggle is found to be particularly prone to fogging of the lens. This is because the positioning of the magnets on the lens obstructs the optimal locations for ventilation slits, which in other types of goggles would be provided to avoid fogging.

It is an object of the invention to reduce or substantially obviate the above mentioned problems.

SUMMARY OF THE INVENTION

According to the present invention, there is provided a goggle for use in snowsports, the goggle comprising a flexible frame and a lens assembly, magnets or magnetic elements being provided on upper and lower edges of an inner surface of the lens assembly and magnets or magnetic elements being provided in corresponding positions on an outer surface of the frame, for releasably holding the lens assembly in the frame, and at least two releasable clips being provided on the frame, the clips being movable between a released position and an engaged position, the clips in the engaged position overlying a portion of the lens assembly and each clip including at least one retaining member which in use passes into an aperture at least part way through the lens assembly, in a direction substantially perpendicular to the surface of the lens assembly, for preventing or limiting movement of the lens assembly in a direction away from the lateral side of the frame.

The goggle of the invention provides for a quick-release lens system which is nevertheless robustly held together and does not easily fall apart in a collision. The clips prevent sideways movement of the lens, and significantly reduce the risk that twisting forces on the frame will cause the frame to be detached from the lens.

In different embodiments, magnets may be provided on both of the lens assembly and the frame, or alternatively magnets may be provided on only one of the two components, the other including, for example, pieces of steel or another magnetic material which is not itself permanently magnetized.

Preferably, the clips are provided on each lateral side of the frame.

In one embodiment, the clips are hinged to the frame and movable on the hinge between the engaged and released positions. In the released position, the clips lift away from the lens assembly allowing the lens assembly to be removed. In the engaged position, the clips overlie the lens assembly to obstruct removal of the lens assembly.

The retaining member is preferably in the form of a tang having a proximal end attached to the body of the clip and a distal end. The distal end preferably includes a resilient detent. When the retaining member passes through the aperture of the lens assembly, the detent may pass over an edge of the aperture and grip against the lens assembly from a back side of the aperture.

Preferably, lugs are provided on one of the lens assembly and the frame, for interfacing with indents or apertures on the other of the lens assembly and the frame. For example, there may be lugs on the lens assembly and indents on the frame, or lugs on the frame and indents on the lens assembly. In some embodiments, lugs on the lens assembly for interfacing with indents on the frame may be provided as well as lugs on the frame for interfacing with indents on the lens assembly.

The lugs help to position the lens assembly on the frame, and also further assist in making the assembled goggle resistant to twisting forces. Preferably, lugs and/or indents are provided on the upper and lower edges of the lens assembly, and in corresponding positions on the frame, and the lugs and/or indents may be provided substantially in-line with the magnets and/or magnetic elements.

Alternatively or additionally, positioning elements may be provided on the frame, for placing against the edge of the lens assembly when the lens assembly is positioned on the frame. Preferably, a cut out is provided in one or more corners of the lens assembly, for placing against the positioning elements. The positioning elements therefore prevent movement of the frame in substantially two perpendicular directions. When the goggle is in its normal orientation (i.e. on the face of a wearer) the two perpendicular directions are approximately horizontal and vertical.

According to a second aspect of the invention, there is provided a goggle for use in snowsports, the goggle comprising a flexible frame and a lens assembly, magnets or magnetic elements being provided on upper and lower edges of an inner surface of the lens assembly and magnets or magnetic elements being provided in corresponding positions on an outer surface of the frame, for releasably holding the lens assembly in the frame, the lens assembly including a lens frame, an outer lens bonded to an outward surface of the lens frame, and an inner lens bonded to an inward surface of the lens frame, and at least one venting aperture provided on the upper edge of the lens assembly for allowing air to pass through the lens assembly, the venting aperture passing through the outer lens and the lens frame, and the inner lens being bonded to the lens frame with the upper edge of the inner lens positioned on the lens frame below the venting aperture.

The arrangement of the second aspect of the invention allows for ventilation in a magnetically-attachable double-lens assembly, reducing fogging of the lens in use. The magnets and/or magnetic elements on the lens assembly may be positioned on the inward side of the lens frame, and the magnets/magnetic elements on the upper edge may be substantially in-line with the venting aperture(s).

It will be understood that features of the first aspect of the invention may be incorporated into embodiments of the second aspect of the invention, and vice versa.

BRIEF DESCRIPTION OF THE DRAWINGS

For a better understanding of the present invention, and to show more clearly how it may be carried into effect, a preferred embodiment will now be described, by way of example only, with reference to the accompanying drawings in which:

FIG. 2 is a plan view from one side of the ski goggle of FIG. 1;

FIG. 3 is a close-up perspective view of part of the goggle of FIG. 1, showing in particular positioning elements on the frame and a cut-away in corners of the lens assembly;

DETAILED DESCRIPTION OF THE INVENTION

Figure 1:
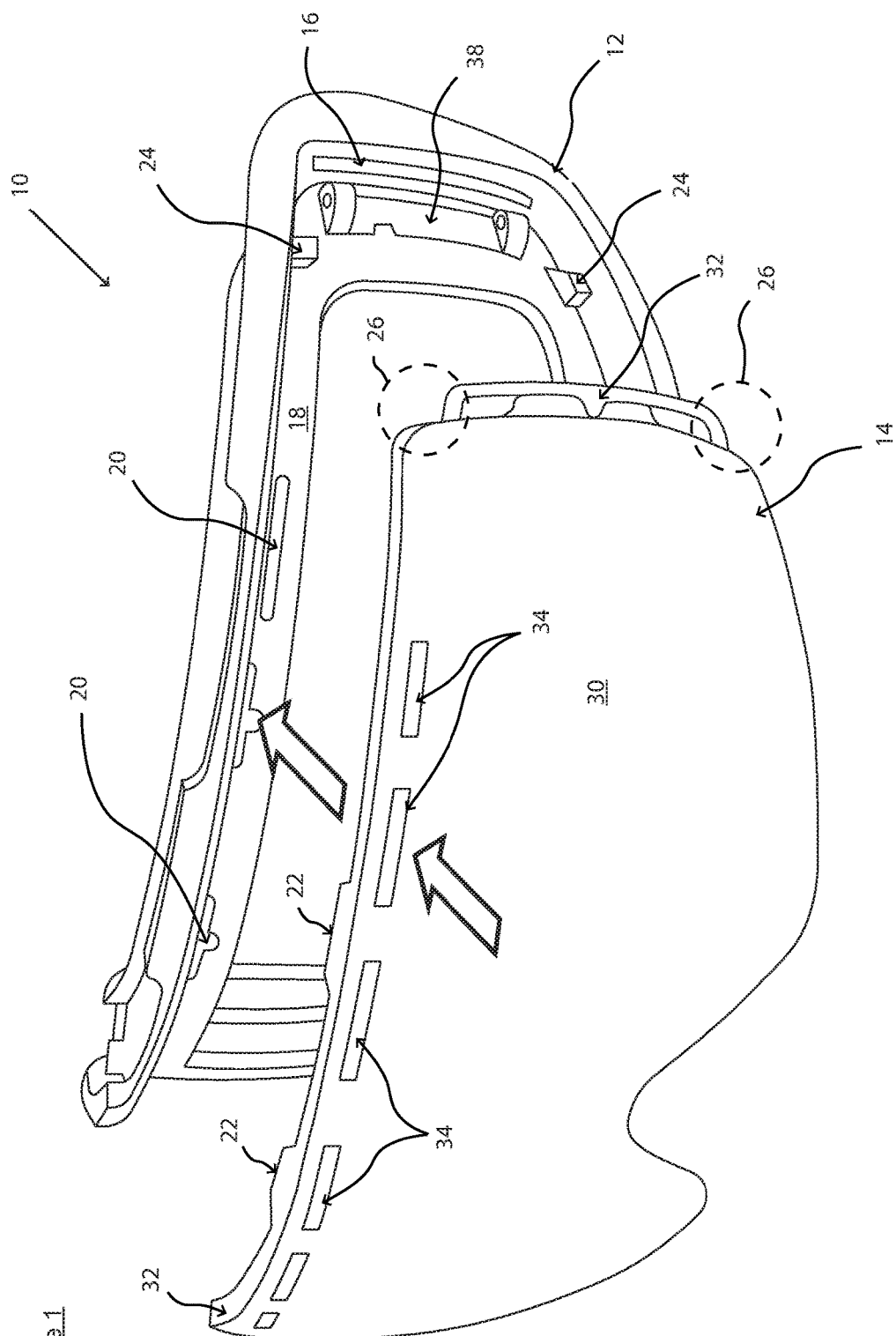
FIG. 1 is a schematic perspective view of a ski goggle comprising a frame and a lens assembly.

Referring firstly to FIG. 1, a goggle for use in snowsports is indicated generally at 10. The goggle includes a frame 12 and a lens assembly 14.

The frame is made from a flexible plastics material and is shaped to conform with the face of a wearer. The back of the frame includes a soft padding for placing against the face, and an attachment 16 for a strap is provided on either lateral side of the frame. The frame includes a flange 18 forming part of the front surface of the frame, for accepting and placing against the lens assembly 14. The flange 18 includes indents 20 for receiving lugs 22 on the lens assembly 14, and positioning elements 24 for placing against cut-aways 26 on the corners of the lens assembly 14.

Magnets (28) are also positioned around the flange, for attracting corresponding magnets on the upper and lower edges of the inner surface of the lens assembly 14.

The lens assembly 14 is a double-lens, i.e. an inner lens and an outer lens 30. The outer lens 30 is visible in FIG. 1. The outer lens 30 is bonded to and substantially overlies a lens frame 32, only edges of which are visible in the Figure. Venting apertures 34 are provided along an upper edge of the lens assembly 14. The venting apertures pass through both the outer lens 30 and the lens frame. The inner lens (36) is smaller than the outer lens 30, and in particular the top edge of the inner lens is bonded to the lens frame 32 at a position below the venting apertures 34, as shown in the Figure and as positioned in normal use.

Referring now to FIG. 2, certain features of the frame 12 and lens assembly 14 are visible in greater detail. In particular, the extent of the outer lens 30 compared with the lens frame 32 and the inner lens 36 is clear. The inner lens 36 is smaller and is positioned inward of a majority of the inward surface area of the lens frame 32. The outer lens 30 is larger and substantially covers the lens frame 32 as viewed from the front.

The lugs 22 and corresponding indents 20 are also shown in FIG. 2. Also, some of the magnets 28 on the flange 18 of the frame are shown. Two magnets 28 positioned on the upper and lower sides of the flange 18 are visible in FIG. 2, but in this embodiment there are six magnets in total—the view from the other side is a mirror image of FIG. 2 and two further magnets are in corresponding positions on the left hand side of the filter as viewed from in front, and a further two magnets are disposed on the upper and lower sides of the flange 18, substantially centrally between the two lateral sides of the goggle 10. Corresponding magnets are provided in corresponding positions on the lens frame 32, above and below the inner lens 36 and substantially horizontally in-line with the venting apertures 34, for attracting the magnets 28 on the flange 18 of the frame 12.

A mount 38 for a hinged clip is also shown in FIGS. 1 and 2. The mount 38 is in the form of a pair of supports extending perpendicularly in a forward/outward direction away from the outward surface of the flange 18. The supports each include an aperture which can pivotally receive a pin of a hinged clip, so that the hinged clip may pivot "open" and laterally sideways away from the goggle to release the lens, or "closed" towards the centre of the goggle to overlie and retain the lens in position.

FIG. 3 shows the positioning elements 24 in closer detail, as well as the cut-outs 26 on the corners of the lens assembly 14. Note that, for clarity, the hinge mount 38 is omitted from FIG. 3. The corner cut-outs 26 are in the lens frame 32, and together ensure that any horizontal or vertical (in the directions marked x and y in the Figure) movement of the lens assembly 14 with respect to the frame 12 is prevented. The lens frame 32 extends laterally sideways, out from behind the outer lens 30, and includes a pair of apertures 40 for receiving retaining members on a hinged clip.

Figure 4A:
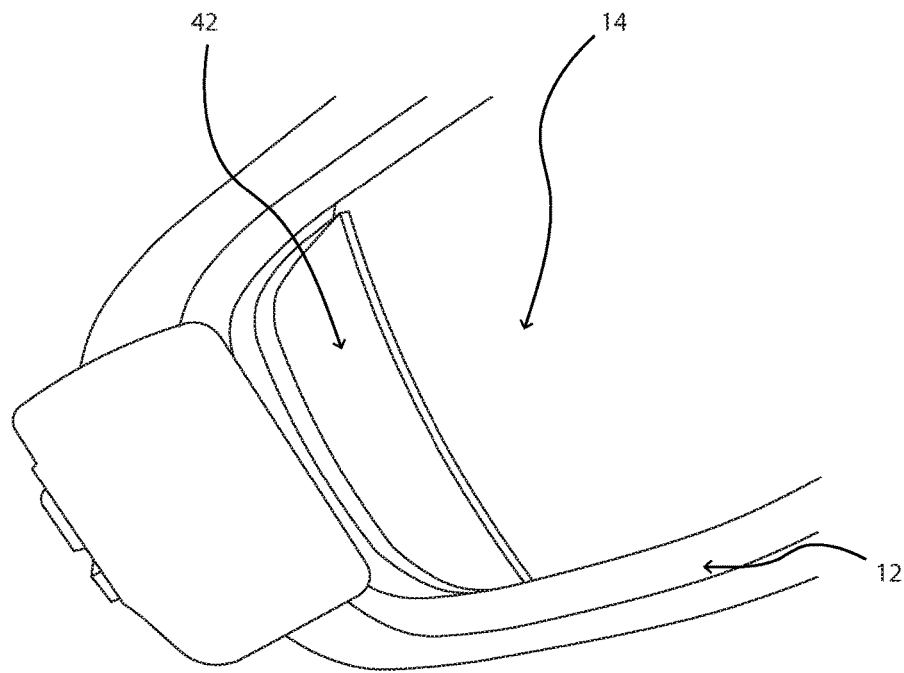
FIG. 4a is a close-up perspective view of part of the goggle of FIG. 1, showing in particular a clip at a lateral side of the frame for holding the lens assembly in position, the clip shown in this Figure in an engaged position.
Figure 4B:
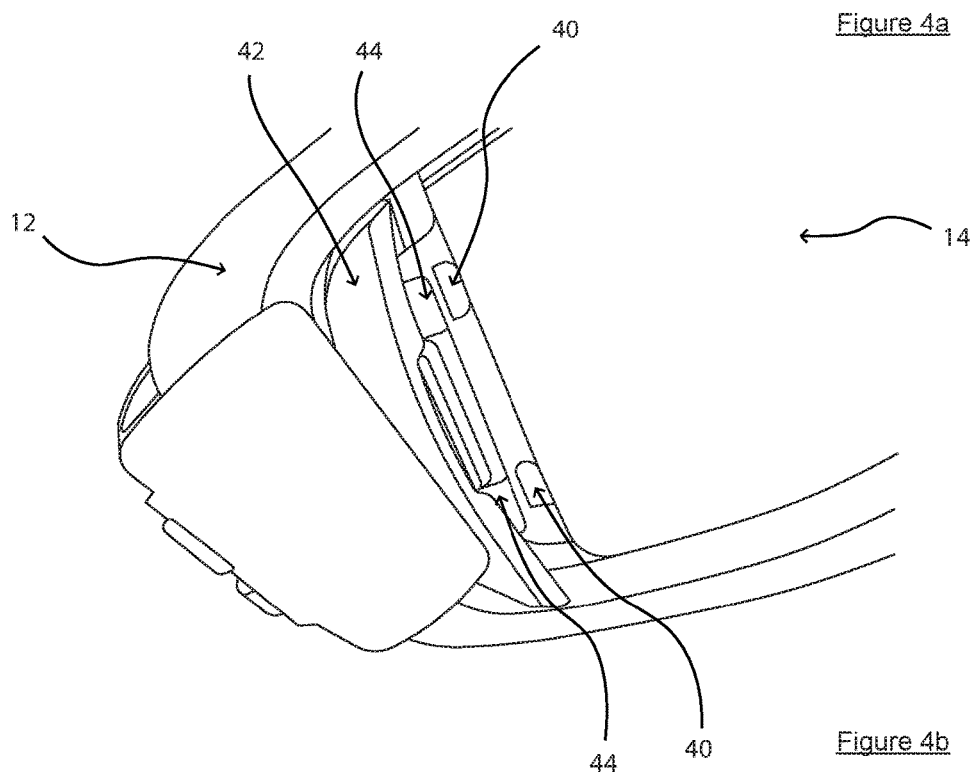
FIG. 4b is a close-up perspective view of part of the goggle of FIG. 1, showing the clip of FIG. 4a in a released position.

FIGS. 4a and 4b show a hinged clip 42 which is mounted on the hinge mount (38) and can be pivoted to overlie and engage the lens assembly 12 (in FIG. 4a), or to release and sit clear of the lens assembly 12 (in FIG. 4b). The clip 42 includes a pair of retaining members 44 which, when the clip is engaged, pass through the apertures 40 on the lens frame 32. As the hinged clips 42 are pivoted into their engaged position, the back faces of the retaining members 44 (i.e. the face which is hidden in FIG. 4b) push against the interior surfaces of the apertures 40, in a camming action, to pull the lens assembly 14 towards the lateral side of the frame 12, and to prevent movement of the lens assembly away from the lateral sides. With both clips (on either lateral side) engaged, the lens assembly 14 is in effect slightly stretched over the frame 12.

Each retaining member, in this embodiment, is in the form of a resilient tang, having a lip at its distal end which faces towards the centre of the goggle when the clips are engaged. The lip grips against an inner surface of the aperture 40, preventing the clip from falling out of the engaged position into the released position without a positive force being applied manually.

The combination of the magnets, lugs, positioning elements and hinged clips provides for a better goggle for snowsports, where the lens can be changed quickly but will not easily come loose in a collision. In addition, the construction of the lens assembly uniquely allows for ventilation, preventing fogging, in a goggle with a magnetic attachment.

The embodiments described above are provided by way of example only, and various changes and modifications will be apparent to persons skilled in the art without departing from the scope of the present invention as defined by the appended claims.

The invention claimed is:

1. A goggle for use in snowsports, the goggle comprising:
a flexible frame and a lens assembly,
magnets or magnetic elements being provided on upper and lower edges of an inner surface of the lens assembly and magnets or magnetic elements being provided in corresponding positions on an outer surface of the frame, for releasably holding the lens assembly in the frame, and
at least two releasable clips being provided on the frame, the clips being pivotable between a released position and an engaged position, the clips in the engaged position overlying a portion of the lens assembly and each clip including at least one retaining member which in use passes into an aperture at least part way through the lens assembly, in a direction substantially perpendicular to the surface of the lens assembly, for preventing or limiting movement of the lens assembly in a direction away from the lateral side of the frame wherein the clips are hinged to the frame and movable on the hinge between the engaged and released positions.

2. The goggle of claim 1, wherein the magnets are provided on both of the lens assembly and the frame.

3. The goggle of claim 1, wherein the magnets are provided on only one of the lens assembly and frame, and pieces of steel or another magnetic material which are not permanently magnetized are attached to the other of the lens assembly and frame.

4. The goggle of claim 1, wherein the clips are provided on each lateral side of the frame.

5. The goggle of claim 1, wherein the retaining member is in the form of a tang having a proximal end attached to the body of the clip and a distal end including a resilient detent for passing over an edge of the aperture in the lens assembly and gripping against the lens assembly from a back side of the aperture.

6. The goggle of claim 1, wherein lugs are provided on one of the lens assembly and the frame, for interfacing with indents or apertures on the other of the lens assembly and the frame.

7. The goggle of claim 6, wherein lugs and/or indents are provided on the upper and lower edges of the lens assembly and in corresponding positions on the frame.

8. The goggle of claim 6, wherein lugs and/or indents are provided substantially in-line with the magnets and/or magnetic elements.

9. The goggle of claim 1, wherein positioning elements are provided on the frame, for placing against the edge of the lens assembly when the lens assembly is positioned on the frame.

10. The goggle of claim 9, wherein a cut-out is provided in one or more corners of the lens assembly, for placing against the positioning elements.

11. The goggle of claim 1, wherein the lens assembly includes a lens frame, an outer lens bonded to an outward surface of the lens frame, and an inner lens bonded to an inward surface of the lens frame, and at least one venting aperture provided on the upper edge of the lens assembly for allowing air to pass through the lens assembly, the venting aperture passing through the outer lens and the lens frame, and the inner lens being bonded to the lens frame with the upper edge of the inner lens positioned on the lens frame below the venting aperture.

12. The goggle of claim 11, wherein the magnets and/or magnetic elements on the lens assembly are positioned on the inward side of the lens frame.

13. The goggle of claim 11, wherein the magnets/magnetic elements on the upper edge are substantially in-line with the venting aperture(s).

14. A goggle for use in snowsports, the goggle comprising:
a flexible frame and a lens assembly,
magnets or magnetic elements being provided on upper and lower edges of an inner surface of the lens assembly and magnets or magnetic elements being provided in corresponding positions on an outer surface of the frame, for releasably holding the lens assembly in the frame, and
at least two releasable clips being provided on the frame, the clips being movable between a released position and an engaged position, the clips in the engaged position overlying a portion of the lens assembly and each clip including at least one retaining member which in use passes into an aperture at least part way through the lens assembly, in a direction substantially perpendicular to the surface of the lens assembly, for preventing or limiting movement of the lens assembly in a direction away from the lateral side of the frame,
wherein the retaining member is in the form of a tang having a proximal end attached to the body of the clip and a distal end including a resilient detent for passing over an edge of the aperture in the lens assembly and gripping against the lens assembly from a back side of the aperture,
and wherein the lens assembly includes a lens frame, an outer lens bonded to an outward surface of the lens frame, and an inner lens bonded to an inward surface of the lens frame, and at least one venting aperture provided on the upper edge of the lens assembly for allowing air to pass through the lens assembly, the venting aperture passing through the outer lens and the lens frame, and the inner lens being bonded to the lens frame with the upper edge of the inner lens positioned on the lens frame below the venting aperture wherein the clips are hinged to the frame and movable on the hinge between the engaged and released positions.

15. The goggle of claim 14, wherein the magnets and/or magnetic elements on the lens assembly are positioned on the inward side of the lens frame.

16. The goggle of claim 14, wherein the magnets/magnetic elements on the upper edge are substantially in-line with the venting aperture(s).

\* \* \* \* \*